United States Patent
Yoon

(10) Patent No.: US 6,988,801 B2
(45) Date of Patent: Jan. 24, 2006

(54) COMPACT PORTABLE WAVEFRONT SENSOR

(75) Inventor: Geunyoung Yoon, Pittsford, NY (US)

(73) Assignee: University of Rochester, Rochester, NY (US)

( * ) Notice: Subject to any disclaimer, the term of this patent is extended or adjusted under 35 U.S.C. 154(b) by 314 days.

(21) Appl. No.: 10/397,101

(22) Filed: Mar. 25, 2003

(65) Prior Publication Data

US 2004/0189942 A1 Sep. 30, 2004

(51) Int. Cl.
*A61B 3/10* (2006.01)
*A61B 3/14* (2006.01)

(52) U.S. Cl. .................... 351/221; 351/205; 351/206
(58) Field of Classification Search ........... 351/200, 351/205, 211–215, 221, 246
See application file for complete search history.

(56) References Cited

U.S. PATENT DOCUMENTS

| | | | |
|---|---|---|---|
| 4,413,890 A | 11/1983 | Belkin et al. | |
| 4,744,649 A | 5/1988 | Niino et al. | |
| 5,090,795 A | 2/1992 | O'Meara et al. | |
| 5,125,730 A | 6/1992 | Taylor et al. | |
| 5,329,322 A | 7/1994 | Yancey | |
| 5,479,221 A | 12/1995 | Heine et al. | |
| 5,777,719 A | 7/1998 | Williams et al. | |
| 5,861,938 A | 1/1999 | Heacock | |
| 5,943,117 A | 8/1999 | Van de Velde | |
| 5,949,521 A | 9/1999 | Williams et al. | |
| 6,027,216 A | 2/2000 | Guyton et al. | |
| 6,053,613 A | * 4/2000 | Wei et al. | 351/205 |
| 6,079,830 A | 6/2000 | Kohayakawa | |
| 6,095,651 A | 8/2000 | Williams et al. | |
| 6,157,498 A | * 12/2000 | Takahashi | 359/728 |
| 6,264,328 B1 | 7/2001 | Williams et al. | |
| 6,276,800 B1 | 8/2001 | Baker | |
| 6,299,311 B1 | 10/2001 | Williams et al. | |
| 6,379,005 B1 | 4/2002 | Williams et al. | |
| 6,550,917 B1 | * 4/2003 | Neal et al. | 351/221 |
| 2003/0025874 A1 | 2/2003 | Williams et al. | |

FOREIGN PATENT DOCUMENTS

EP 0 221 649 5/1987

* cited by examiner

Primary Examiner—Brian Casler
Assistant Examiner—John R. Sanders
(74) Attorney, Agent, or Firm—Knobbe Martens Olson & Bear LLP

(57) ABSTRACT

A device measures aberrations of an eye and contains a first light source, a lens, a reflective surface, and a wavefront sensor. The first light source is adapted to reflect light off eye's retina to produce a wavefront. The lens is adapted to receive light from the wavefront. The reflective surface is disposed so as to reflect light from the wavefront that is received by the lens back through the lens to produce an image of the wavefront. The wavefront sensor is adapted to receive light from the wavefront so as to provide a measure of the aberrations of the eye. The device may contain a second light source primarily at a second wavelength that illuminates the eye. Light from the second light source is substantially transmitted through the reflective surface to form an image of the eye that may be used to align the device.

30 Claims, 6 Drawing Sheets

COMPACT PORTABLE WAVEFRONT SENSOR

BACKGROUND OF THE INVENTION

1. Field of the Invention

The present invention is directed to a wavefront measuring device, and more specifically, to wavefront sensor for measuring ocular aberrations.

2. Description of the Related Art

Ocular aberrations are typically the result of variations in the eye's lens and cornea which preclude the points on an object from uniformly coming to a sharp focus on the retina of the eye. Various refractive techniques have been used to correct ocular aberrations, such as the external eye glasses or contact lenses. For such corrective methods, interaction by the patent is generally available to the practitioner for determining the appropriate level of correction. Once the required amounts of spherical and cylindrical correction are determined, corrective lenses are made to restore visual acuity. In recent years, the field of ophthalmology has also developed more advanced techniques, such as Photorefractive Keratectomy (PRK), Laser Epithelial Keratomileusis (LASEK), and Laser-Assisted In-Situ Keratomileusis (LASIK), which allow the practitioner to directly modify the shape of the cornea to restore visual acuity.

Eye glasses and contact lenses generally correct only for ocular defocus and astigmatism. A wavefront sensor is a device that allows characterization of a wavefront in order to determine deviations in the wavefront from an idealized wavefront profile. The use of wavefront sensors offers the possibility of identifying and correcting additional ocular aberrations such as coma, sphere, and other higher order aberrations. Using a wavefront sensors also allows the practitioner to objectively quantify the amount of ocular aberrations without patient interaction.

In one approach, a Shack-Hartmann type wavefront sensor is used to measure ocular aberrations by first focusing light onto the retina by using the eye's own cornea and lens. The focused spot on the eye acts as a point source that illuminates the lens and cornea from behind to produce a wavefront that may be examined using the wavefront sensor to measure ocular aberrations. The Shack-Hartmann wavefront sensors are commonly used to measure ocular aberrations, since such sensors do not require a coherent light source and is, therefore, robust to vibrations. Other benefits of the Shack-Hartmann sensor in ocular applications include (1) the measurement is typically very fast because single frame includes all the information needed to calculate wavefront aberration and (2) measurement performance is not sensitive to other system aberrations since these aberrations can calibrated out by using reference spot array pattern.

A typical Shack-Hartmann wavefront sensor based device for ocular applications is disclosed by Williams and the present inventor in U.S. Pat. No. 6,264,328, which is hereby incorporated by reference. Using the device disclosed by Williams et. al., light from a light source is focused onto the retina of an eye. Light reflected by the retina passes back through the lens and cornea of the eye produces an aberrated wavefront in front of the eye. A pair of imaging lenses are used to transfer an image of the wavefront to a Shack-Hartman or equivalent wavefront sensor using the pair of lenses. There exist a need to reduce the size and increase the durability in this and similar types of instruments used in the measurement of ocular wavefronts.

SUMMARY OF THE INVENTION

A device for measuring ocular wavefronts, such as that disclosed by the U.S. Pat. No. 6,264,328, may be reduced by utilizing a double-pass configuration in which a single lens is used twice. The double-pass configuration utilizes a reflective surface disposed at or near the focus of the wavefront as it makes a first pass through the lens. The focused light then reflected back to the lens during the second pass to produce the image of the wavefront. By utilizing the space between the lens and the reflective surface twice, a more rugged and compact instrument results that is well suited for detection and correction of ocular aberrations.

One aspect of the invention comprises a device for measuring aberrations of an eye. The device comprises a first light source, a lens, and a reflective surface. The first light source is adapted to reflect light off the retina of the eye so as to produce a wavefront that propagates along an optical path. The lens is adapted to receive light from the wavefront. The reflective surface is disposed so as to reflect light from the wavefront that is received by the lens back through the lens, so as to produce an image of the wavefront. A wavefront sensor may be adapted to receive light from the wavefront that is reflected back through the lens so as to provide a measure of the aberrations of the eye. The first light source may be a laser or similar such light source and the wavefront sensor may be of a Shack-Hartmann type sensor. The reflective surface is preferably deposed at or near a focus of the lens and may be movable so as to allow adjustment of the distance between the focus and the reflective surface.

In another aspect of the invention, the device further comprises wavefront directing optics. The wavefront directing optics may comprise a beamsplitter that is disposed along the optical path between the eye and the lens. The beamsplitter is adapted to transmit light from the wavefront propagating from the eye to the beamsplitter and to reflect light from the wavefront propagating from the reflective surface to the beamsplitter.

In another aspect of the present invention, the device comprises a second light source disposed to illuminate the eye. The first light source provides light primarily at a first wavelength, while the second light source provides light primarily at a second wavelength, different from the front wavelength. In such configurations, the reflective surface may comprise a dichroic filter. The reflective surface reflects light from the first light source and transmits light from the second light source. A camera may be adapted to receive light from the second light source that is reflected off at least a portion of the eye. The camera is adapted to produce an image of the eye and the image of the eye is used to provide alignment between the wavefront sensor and the eye. Preferably, the image of the eye include the eye's pupil and at least a portion of the eye's iris.

In still another aspect of the present invention, a method of measuring aberrations of an eye comprises illuminating the eye with light primarily at a first wavelength so as to produce a wavefront that propagates along an optical path. The method further comprises providing a lens for receiving a light from the wavefront. The method further comprises reflecting light received by the lens off of a reflective surface. The method also comprises transmitting light reflected off the reflective surface back through the lens so as to form an image of the wavefront. The method additionally comprises providing a wavefront sensor that is adapted to provide a measure of the aberrations of the eye.

Another aspect of the present invention comprises a method of aligning the wavefront sensor to the eye. The method comprises illuminating the eye with light primarily at a second wavelength, different from the first wavelength. The method additionally comprises reflecting light primarily at the second wavelength off the eye. The method additionally comprises transmitting the light reflected off the eye through the reflective surface. The method also comprises producing an image of the eye on a camera and aligning the wavefront sensor to the eye based on the location of the image of the eye within the camera. Preferably, the image of the eye include the eye's pupil and at least a portion of the eye's iris.

BRIEF DESCRIPTION OF THE DRAWINGS

The foregoing features, aspects, and advantages of the present invention will now be described with reference to the drawings of preferred embodiments that are intended to illustrate and not to limit the invention. The drawings comprise four figures.

DETAILED DESCRIPTION OF THE PREFERRED EMBODIMENT

These and other embodiments of the present invention will also become readily apparent to those skilled in the art from the following detailed description of preferred embodiments having reference to the attached figures; however, the invention is not limited to any particular embodiment(s) disclosed herein. Accordingly, the scope of the present invention is intended to be defined only by reference to the appended claims.

Figure 1:
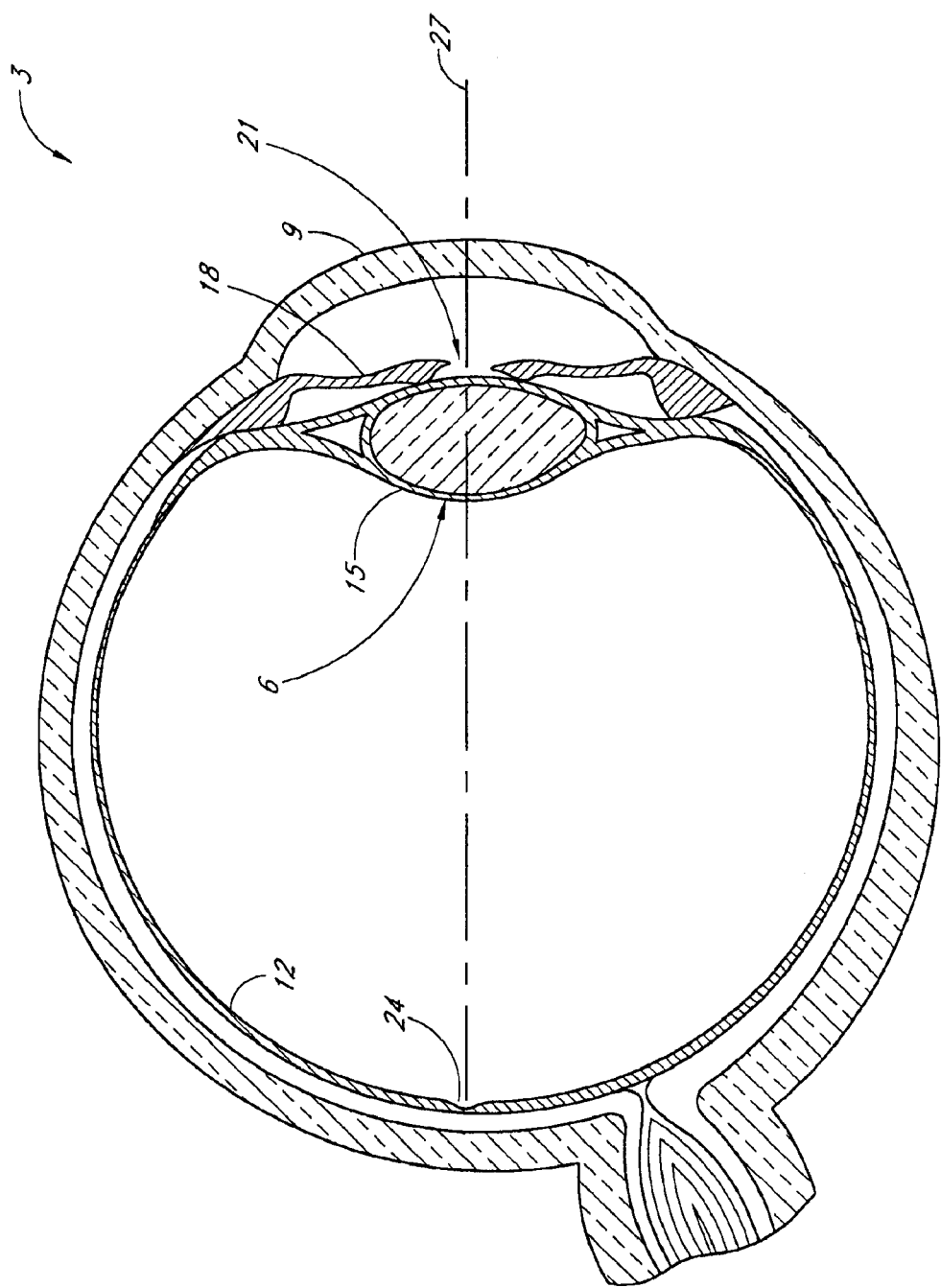
FIG. 1 is a schematic illustration of the anatomy of the eye including the cornea, iris, and lens.

As is well known and illustrated in FIG. 1, an eye 3 includes an ocular lens 6 and a cornea 9 at the front of the eyeball and a retina 12 located at the back of the eyeball. An image is formed on the retina 12 by the combined refractive power of the ocular lens 6 and a cornea 9. This ocular lens 6 is held in place by the ciliary body 15 and fibrous muscle included therewith. An iris 18, disposed on an anterior surface of the ocular lens 6, comprises an opaque tissue and includes a central opening, commonly referred to as the pupil 21. A tiny region approximately at the center of the retina 12, known as the fovea 24, comprises densely packed photoreceptors, which provide vision for fine detail. When the eye 3 peers at a distant object, the eye 3 rotates until an image of the distant object falls on the fovea 24. A straight line drawn through the center of the pupil 21 and the fovea 24 is known as the visual axis 27, sometimes referred to as the line of sight.

Figure 2:
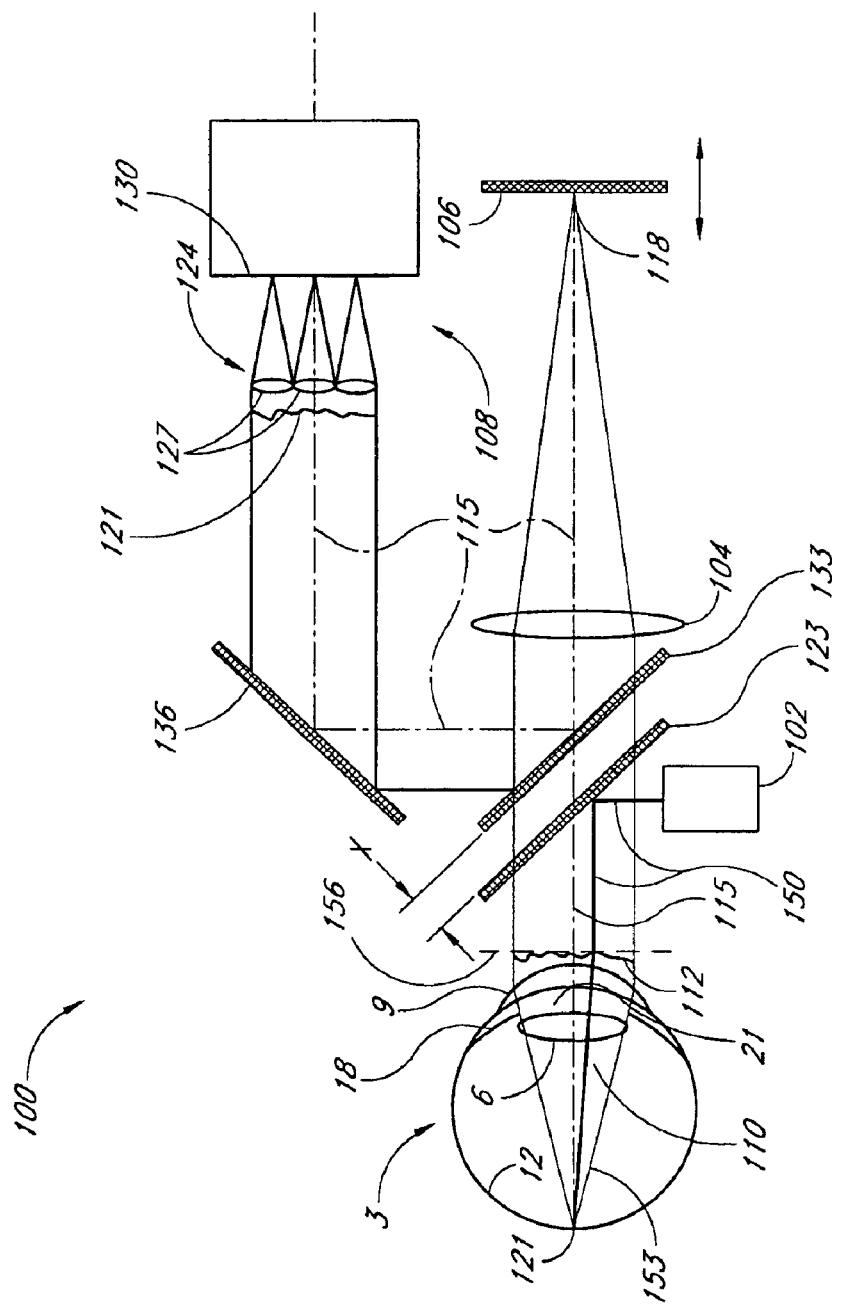
FIG. 2 is a schematic illustration of a device according to embodiments of the invention, wherein a single lens is used twice to produce an image of a wavefront for use by a wavefront sensor.

In certain embodiments, as illustrated in FIG. 2, a device 100 for measuring aberrations of an eye 3 comprises a first light source 102, a lens 104, and a reflective surface 106. The first light source 102 is adapted to reflect light off the retina 12 of the eye 3 so as to produce a wavefront 112. The wavefront 112 propagates along an optical path 115. The lens 104 receives the light from the wavefront 112. The reflective surface 106 is disposed to reflect the light from the wavefront 112 and the light that is received by the lens 104 is reflected back through the lens 104, so as to produce an image 121 of the wavefront 112. A wavefront sensor 108 may be adapted to receive the light from the wavefront 112 that is reflected back through the lens 104 so as to provide a measure of the aberrations of the eye 3. The image 121 of the wavefront 112 may also be referred to simply as the wavefront 121. In certain embodiments, the reflective surface 106 is disposed at or near a focus 118 of the lens 104.

As described in further detail below herein, the light from the first light source 102 may be substantially focused onto the retina 12 by the ocular lens 6 and the cornea 9 to produce a point source 121. The reflected light 110 comprises at least a portion of the light that emanates from the point source 121. The point source 121 is so named because light focused by the ocular lens 6 and the cornea 9 generally produces a spot with a diameter that substantially smaller than the diameter of the iris 18 of the eye 3. The size of the point source 121 will depend the diameter of the beam from the first light source 102 when it impinges the eye 3 (i.e., the diffraction limit based on the relationship: spot size= $2.44 * f * \lambda$/beam diameter) and the aberrations produced by the ocular lens 6 and the cornea 9 as beam from the first light source 102 is focused to form the point source 121. Those skilled in the art are able to design the beam diameter of the first light source 102 to produce a small point source 121 based on considerations of diffraction limit and lens aberrations. The point source 121 has a diameter that is preferably less than about 200 micrometers, more preferably less than about 100 micrometers, and even more preferably less than about 20 micrometers. The first light source 102 is preferably a laser, such as a diode laser, having a wavelength that is preferably in the visible or infrared wavebands of the electromagnetic spectrum. However, the first light source 102 may be any light source producing light suitable for focusing onto the retina 12.

In certain embodiments, the device 100 further comprises a first beamsplitter 123 disposed along the optical path 115. The beamsplitter 123 is adapted to reflect a portion of light from the first light source 102 and to direct the reflected portion onto the retina 12 of the eye 3. Optionally, the light from the first light source 102 may be at least partially polarized and the first beamsplitter 123 may be a polarizing beamsplitter. In such embodiments, the polarizing beamsplitter 123 may be used in conjunction with other polarizing components not shown, such as one or more phase retardation plates, to favorably affect the reflection characteristics of the polarizing beamsplitter 123.

The first beamsplitter 123 transmits a portion of light from the wavefront 112. It is desirable in certain embodiments, therefore, that the first beamsplitter 123 be sufficiently transmissive so as to provide an adequate amount of light to the wavefront sensor 108. The amount of light needed by the wavefront sensor 108 depends on many factors including, but not limited to, the transmission of the first beamsplitter 123, the reflectance of the reflective surface 106, the optical characteristics of any wavefront-directing optics along the optical path 115, the sensitivity of wavefront sensor 108 to light, the amount of ambient light entering the wavefront sensor 108, and the algorithms used to process the signal from the wavefront sensor 108. The first beamsplitter 123 is preferably transmits at least 1% of the light from the wavefront 112, more preferably transmits at least 50% of the light from the wavefront 112, and most preferably transmits at least 99% of the light from the wavefront 112. Those skilled in the art are able to select or design the first beamsplitter 123 and the first light source 102 to meet specific requirements such as component costs, the amount of light needed by the wavefront sensor 108, and toleration by the eye 3 to the intensity of light in the point source 122.

The lens 104 serves at least two purposes: (1) to converge or focus light from the wavefront 112, and (2) to form the image 121 of the wavefront 112 from light reflected by the reflective surface 106. Preferably, the distance between the lens 104 and the front of eye 3 is approximately one focal length of the lens 104. The focal length of the lens 104 may be selected such that an unacceptable amount of aberrations are not added to the wavefront 112 when forming the image 121 of the wavefront 112. For instance, in certain embodiments, the lens 104 is a plano-convex or an achromat lens and the distance between the wavefront 112 and the lens 104 is approximately one focal length of the lens 104. In other embodiments, the shape of at least one of the surfaces of the lens 104 is aspheric and the lens 104 is disposed relative to the wavefront 112 such that the lens 104 does not add an unacceptable amount of aberrations to the image 121 of the wavefront 112. In yet other embodiments, the lens 104 is any optical element that converges incident light such as, for example, a concave mirror, a diffractive optical element, or a holographic optical element. In certain embodiments, packaging constraints are weighed against image quality requirements when selecting the type, location, and orientation of the lens 104. Those skilled in the art are able to select the lens 104 and the location and orientation thereof in accordance with particular design parameters.

In certain embodiments, the wavefront sensor 108 is a Shack-Hartmann sensor comprising an array 124 of lenslets 127. Each of the lenslets 127 samples a portion of the wavefront 121 and focuses that portion to a location on a sensor 130. Preferably, the sensor 130 is a two dimensional electronic sensor, such as a charge coupled device (CCD) or a complementary metal oxide semiconductor (CMOS) detector array. As is well known in the art, the nominal slope of the wavefront 121 across each portion or lenslet 127 may be correlated to the location of the focused light on the sensor 130.

In certain embodiments, the device 100 comprises wavefront-directing optics for directing the light from the wavefront 112 to the wavefront sensor 108. In certain embodiments, such as that schematically illustrated in FIG. 2, the wavefront-directing optics comprise a second beamsplitter 133 disposed along the optical path 115 between eye 3 and the lens 104. In certain embodiments, the second beamsplitter 133 is adapted to transmit light from the wavefront 112 propagating from the eye 3 to the second beamsplitter 133 and to reflect light from the wavefront 112 propagating from the reflective surface 106 to the second beamsplitter 133. In certain other embodiments, the wavefront-directing optics further comprise at least one reflector 136 disposed along the optical path 115 between the second beamsplitter 133 and the wavefront sensor 108.

The second beamsplitter 133 preferably transmits more than about 1% and less than 99% of light propagating from the wavefront 112, more preferably transmits more than about 40% and less than about 60% of light propagating from the wavefront 112, and most preferably transmits about 50% of light propagating from the wavefront 112. As illustrated in FIG. 2, the second beamsplitter 133 is separated from the first beamsplitter 123 by a distance x. The distance x is preferably large enough so that light transmitted by the first beamsplitter 123 from the first light source 102 does not enter the wavefront sensor 108 from along the optical path 115. Alternatively, the distance x is smaller than this amount and light from the first light source 102 is filtered out using other means, is received by the wavefront sensor 108 and ignored, or electronically reduced or eliminated. In such embodiments, the two beamsplitters 123, 133 may be combined into a single beamsplitter.

Figure 3:
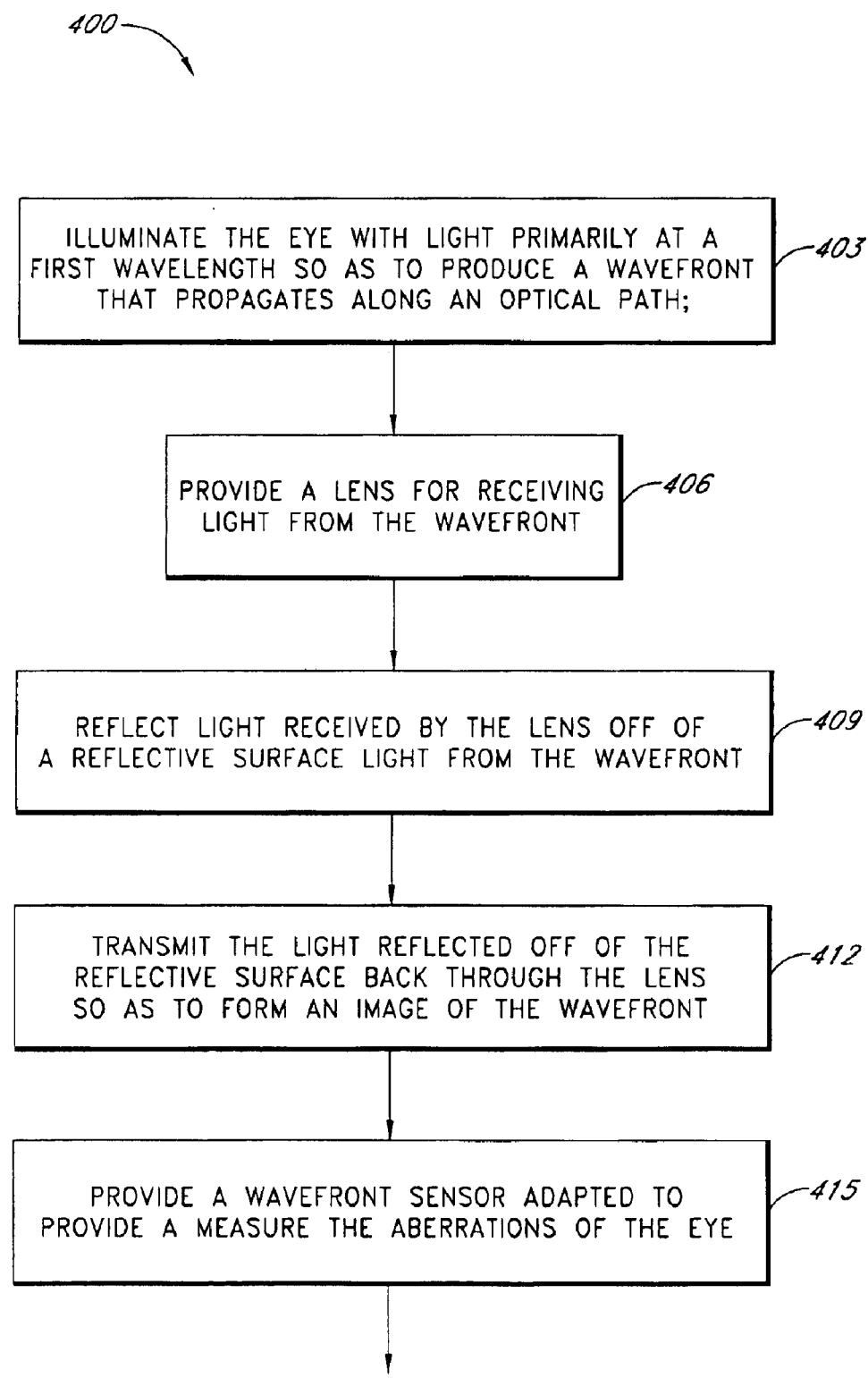
FIG. 3 is a flow diagram of a method of measuring aberrations of an eye in accordance with embodiments of the present invention.

The device 100 may be used to measure aberrations of the eye 3. For example, FIG. 3 is a flow diagram of a method 400 of measuring aberrations of an eye in accordance with embodiments of the present invention. The method 400 is illustrative and does not preclude the use of other methods of measuring aberrations of an eye consistent with embodiments of the present invention.

Referring to FIGS. 2 and 3, the method 400 comprises an operational block 403 which comprises illuminating the eye 3 with the light primarily at a first wavelength $\lambda_1$ so as to produce the wavefront 112 that propagates along the optical path 115. The method 400 further comprises an operational block 406 which comprises providing the lens 104 along the optical path 115 for receiving light from the wavefront 112. The method 400 further comprises an operational block 409 which comprises reflecting light received by the lens 104 off of the reflective surface 106. The method 400 further comprises an operational block 412 which comprises transmitting the light reflected off of the reflective surface 106 back through the lens 104 so as to form an image 121 of the wavefront 112. The method 400 further comprises an operational block 415 which comprises providing the wavefront sensor 108, which is adapted to provide a measure the aberrations of the eye 3. For the embodiment shown in FIG. 2, the light primarily at the first wavelength $\lambda_1$ is provided by the first light source 102.

During illumination with light primarily at a first wavelength $\lambda_1$, the eye 3 of a patient is preferably in an unaccommodated state (i.e., the ocular lens 6 is shaped such that distant objects are substantially in focus on the retina 12 of a normal eye), although the device will also function under other conditions. The patient's eye may be positioned relative to the device 100 using devices and means common in the art, but not shown in the figures for reasons of clarity. For instance, the device 100 may comprise an eyepiece with an aperture disposed at a predetermined position and orientation relative to the device 100. The eye 3 may then be located such that the iris 18 is approximately centered within the aperture of the eyepiece.

Once the eye 3 has been positioned relative to the device 100, the first light source 102 produces a beam of light 150 that illuminates the retina 12 to form the point source 122. The light reflected by the point source 122 located on the retina 12 produces a cone of light 153 defined by light from the point source 122 that passes through the pupil 21 of the iris 18. As light from the point source 122 propagates through the ocular lens 6 and the cornea 9, a distorted or aberrated wavefront 112 is produced outside the eye 3, adjacent to the cornea 9. Any aberrations or imperfections in the ocular lens 6 or the cornea 9 appear in the wavefront 112 as phase deviations from an idealized collimated plane wavefront (i.e., one with constant phase across a plane normal to the direction of propagation).

In the operational block 406 the lens 104 is provided for receiving light from the wavefront 112. The light from the wavefront 112 propagates along the optical axis 115 to the first beamsplitter 123, where at least a portion of the light from the wavefront 112 is transmitted by the first beamsplitter and is received by the lens 104. Preferably, most of the light incident on the first beamsplitter 123 is transmitted. A range of preferred transmissions for the first beamsplitter 123 are discussed above herein. One reason for selecting a high transmission value for the first beamsplitter 123 is for safety considerations regarding potential patient discomfort or damage to the retina 12 if the intensity of the point source 121 exceeds a predetermined level. By using a high transmission value for the beamsplitter 123, most of the light from the point source 121 is transmitted to the wavefront sensor 108. Thus, the amount of intensity of the light in the point source 121 may be kept below the predetermined level while simultaneously accommodating sensitivity requirements of the wavefront sensor 108. By using a first beamsplitter 123 with a high transmission value, most of the light from the retina 12 is available to the wavefront sensor 108 for analysis of the image 121 of the wavefront 112.

When the beamsplitter 123 is highly transmissive, only a small percentage of light from the first light source 102 is generally reflected by the first beamsplitter 123 to form the point source 121 on the retina 12. In such cases, the first light source 102 may be selected with sufficient power so that the intensity of the point source 122 is at or near the predetermined level set by safety consideration for the retina 12. In other embodiments, the sensitivity of the wavefront sensor 108 is sufficiently high so that the intensity of the point source 122 may be well below an upper limit defined by the sensitivity of the retina 12 to light. In yet other embodiments, the first light source 102 is used with other optical components, such as a variable attenuator, to provide a desired intensity of the point source 122.

Figure 4:
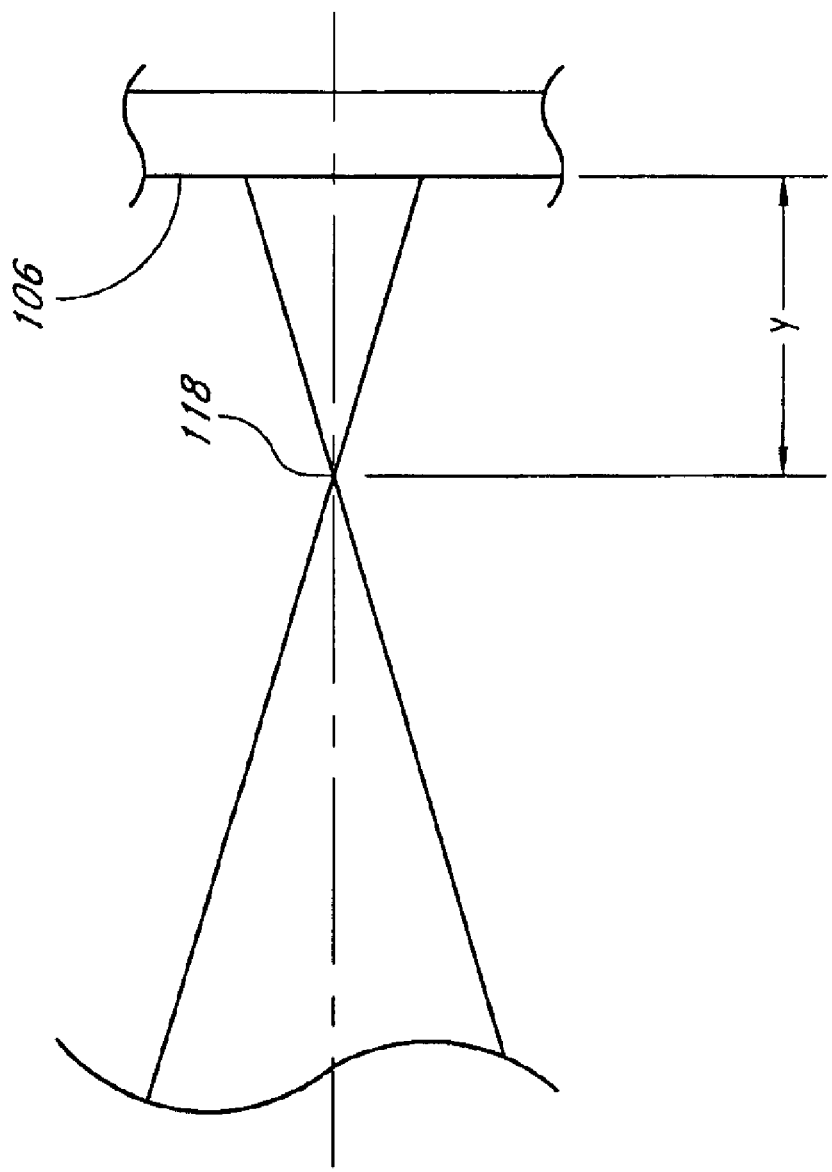
FIG. 4 is a magnified view of a reflective surface showing the position thereof relative to the focus of a lens for a device in accordance with an embodiment of the invention.

In the operational block 409 the light from the wavefront 112 that is received by the lens 104 is reflected off of a reflective surface 106. The lens 104 converges light from the wavefront 112 to form the focus 118. The reflective surface 106 reflects light from the wavefront 112 back towards the lens 104. The distance between the reflective surface 106 and the focus 118 is schematically illustrated in FIG. 4 by the distance y. Preferably, the value of y is approximately zero; however, the device 100 may also be used to measure aberrations of the eye 3 for non-zero values of y.

In certain embodiments, the value of y is defined in terms of the depth of field of the lens 104, which depends on the system f/number defined by the wavefront 112 and the lens 104. For instance, in FIG. 2 the system f/number, $f/\#_{system}$, may be estimated by the relation:

$$f/\#_{system} = f_{lens}/d_{pupil\ diameter} \quad (1)$$

where $f_{lens}$ is the focal length of the lens 104 and $d_{pupil\ diameter}$ is the diameter of the pupil 21 of the eye 3. For a typical adult human eye, the pupil 21 has a diameter when fully dilated of about 7 millimeters; however, this value may vary from about 6.5 millimeters to about 8 millimeters, depending on the age of the subject. The corresponding depth of field is given by the relationship:

$$dof_{system} = \lambda (f/\#_{system})^2 \quad (2)$$

where $\lambda$ is the wavelength of the light in the wavefront 112. Preferably, the magnitude of y is less than approximately ten times ($dof_{system}/2$), more preferably less than approximately plus or minus three times ($dof_{system}/2$), and even more preferably less than approximately ($dof_{system}/2$).

For example, if the device 100 is used with a fully dilated adult human eye with a diameter of 7 millimeters and the lens 104 has a focal length that is 120 millimeters, then $f/\#_{system}$ is approximately 17. As is known in the art, for a system f/number of approximately this value and larger, the system adds substantially no aberrations to the corresponding image (the image 121 of the wavefront 112 in the case of the device 100). If the first light source 102 has a nominal wavelength of 500 nanometers, $dof_{system}$ for the device 100 is approximately 0.15 millimeters, based on Equation 2. Under these conditions, y is preferably less than approximately ±750 micrometer, more preferably less than approximately ±225 micrometers, and even more preferably less than approximately ±75 micrometers.

In other embodiments, the value of y is the result of a calibration procedure wherein the position of the reflective surface 106 is adjusted relative to the location of the focus 118. In one such calibration procedure, the position of the reflective surface is adjusted so that the image 121 of the wavefront 112 is substantially focused onto the array 124 of lenslets 127. If the wavefront sensor 108 is a Shack-Hartmann, the following six-step calibration procedure may be used to position the reflective surface 106 along the optical path 115:

1. Dispose an artificial pupil in the vicinity occupied by the pupil 21 of the eye 3 during a measurement procedure, for example, at a plane 156.
2. Adjust the position of the artificial pupil along the optical axis to a predetermined position using, for instance, a pupil camera.
3. Transmit a collimated beam through the center of the artificial pupil in the direction of the lens 104.
4. Measure the defocus of the image of the artificial pupil using the wavefront sensor 108.
5. Adjust the position of the reflective surface 106 until the defocus is below a predetermined value.
6. Measure the system aberration to determine the amount of residual aberration.

During step (3) through (6) of the above procedure, a spot array pattern is produced on the sensor 130, wherein each spot corresponds to one of the lenslets 127 in the array 124. As is known by those skilled in the art, the spot array pattern may be used to determine the local slopes across a measured wavefront. This data may be used to describe the shape of the wavefront in terms of the coefficients of a Zernike polynomial. The magnitude of the Zernike coefficients corresponds to the aberrations of the wavefront such as defocus, astigmatism, coma, sphere, etc. In steps (4) and (5) the magnitude of the Zernike coefficients may be used to determine and adjust the amount of defocus. The amount of residual aberrations in step (6) may also be determined based on the magnitude of the Zernike coefficients at the end of the alignment procedure.

Other methods and criteria may also be used to adjust the value of y so as the device 100 may be used to measure the aberrations of the eye 3. The above examples for determining the location of the reflective surface 106 should not be construed as limiting, since other configurations and alignment procedures may also be used consistent with embodiments of the present invention.

In the operational block 412 the light reflected off of the reflective surface 106 is transmitted back through the lens 104 to form the image 121 of the wavefront 112. One advantage of the present invention is that it can be produced in the form of a light, compact device, since the space between the lens 104 and the reflective surface 106 is used twice to produce the image 121 of the wavefront 112 (once for focusing the light from the wavefront 112 and once for directing light from the reflective surface 106 to the lens 104). In certain embodiments, the device 100 may be configured to form a hand-held device.

In certain embodiments, the size of the device 100 approximately scales with the focal length of the lens 104. This is approximately the distance between the lens 104 and the reflective surface 106 for the device 100 shown in FIG. 2. The size of the device 100 may have a lower limit due to miniaturization limits for the optical components located between eye 3 and the lens 104. The size of the device 100 may also have a lower limit due to increasing aberrations introduced to the wavefront 112 as the system f/number (i.e., the focal length of the lens 104) is decreased. Based on these considerations, the lens 104 has a focal length that is preferably less than about 1000 millimeters. More preferably, the lens 104 has a focal length of about 120 mm and the device 100 is contained within an envelop that is no larger than about 220 mm in length, 70 mm in width, and 130 mm in height.

In certain embodiments, the lens 104 has a focal length in the range of less than about 120 mm, wherein spherical aberrations may no longer be negligible for a pupil size of approximately 7 millimeters. In such instances, the dynamic range of the device may be reduced or it may be necessary to calibrate the device 100 to maintain a predetermined dynamic range. During calibration of the device 100, the wavefront 112 may be replaced by a substantially collimated beam. In certain embodiments, the lens 104 has a focal length of approximately 60 mm and the device 100 may be contained within an envelop that is approximately 110 in length, 35 millimeters in width, and 65 mm in height.

In the operational block 415, the wavefront sensor 108 is adapted to provide a measure the aberrations of the eye 3. In certain embodiments, the wavefront sensor 108 is a Shack-Hartmann type sensor and the image 121 of the wavefront 112 is received by the array 124 of lenslets 127; however, other types of wavefront sensors may be used in a manner consistent with embodiments of the device 100. As described above herein, wavefront directing optics may be used direct the image 121 of the wavefront 112 to the wavefront sensor 108. For example, as illustrated in FIG. 2, the wavefront directing optics may comprise the second beamsplitter 133 and the reflective surface 136.

In certain embodiments, the method 400 additionally comprises providing wavefront-directing optics for directing the image 121 of the wavefront 112 to wavefront sensor 108. For example, as shown in FIG. 2, the second beamsplitter 133 and the mirror 136 direct the light from the wavefront 112, such that the image 121 of the wavefront 112 is disposed at or near the lenslets 127 of the wavefront sensor 108. The use of such wavefront-directing optics aids in making the device 100 physically realizable and in providing system layout that is contained within an envelope of predetermined dimensions. The use of the second beamsplitter 133 and the mirror 136 in FIG. 2 is exemplary and should not be construed as limiting, since those skilled in the art are able to select and arrange other wavefront-directing optics consistent with embodiments of the present invention.

In certain embodiments, the method 400 additionally comprises moving the reflective surface 106 so as to adjust the distance y between the focus 118 and the reflective surface 106. Preferably, the reflective surface 106 is attached to a translation device (not shown), such as a translation stage having a micrometer. The reflective surface 106 may be moved manually to adjusted the distance y. Alternatively, the translation device may be controlled by an electronic controller, wherein the reflective surface 106 is moved in response to either input from an operator or a computer program that adjust the position of the reflective surface in an automated or semi-automated manner.

In certain embodiments, the method 400 additionally comprises moving the reflective surface 106 so as to compensate for ocular defocus caused by, for example, a myopic nor hyperopic condition. In such embodiments, the distance y is substantially zero for a normal eye (i.e., an eye that is neither myopic nor hyperopic). For an eye 3 that produces an amount of ocular defocus, y has a non-zero value so as to provide a predetermined amount of compensating defocus to the wavefront sensor 108. For example, if the eye 3 has a −4 diopter defocus, this may be corrected by generating +4D defocus in the wavefront sensor 108. In one embodiment, the value of y to obtain a prescribed amount of dioptric correction is given by the relationship:

$$y=-(\Delta y \times f^2)/2, \qquad (3)$$

where y is in units of meters, $\Delta y$ is the amount of dioptric change in units of reciprocal meters, and f is the focal length in units of meters of the lens 104. The negative sign is used so that y is positive when the reflective surface 106 is moved away from the lens and negative when the reflective surface 106 is moved toward the lens 104. For example, to correct myopic (near-sighted) eye that has negative dioptric power, the reflective surface 106 is moved toward the lens 104 (i.e., y is negative) to generate positive optical power, $\Delta y$.

Figure 5:
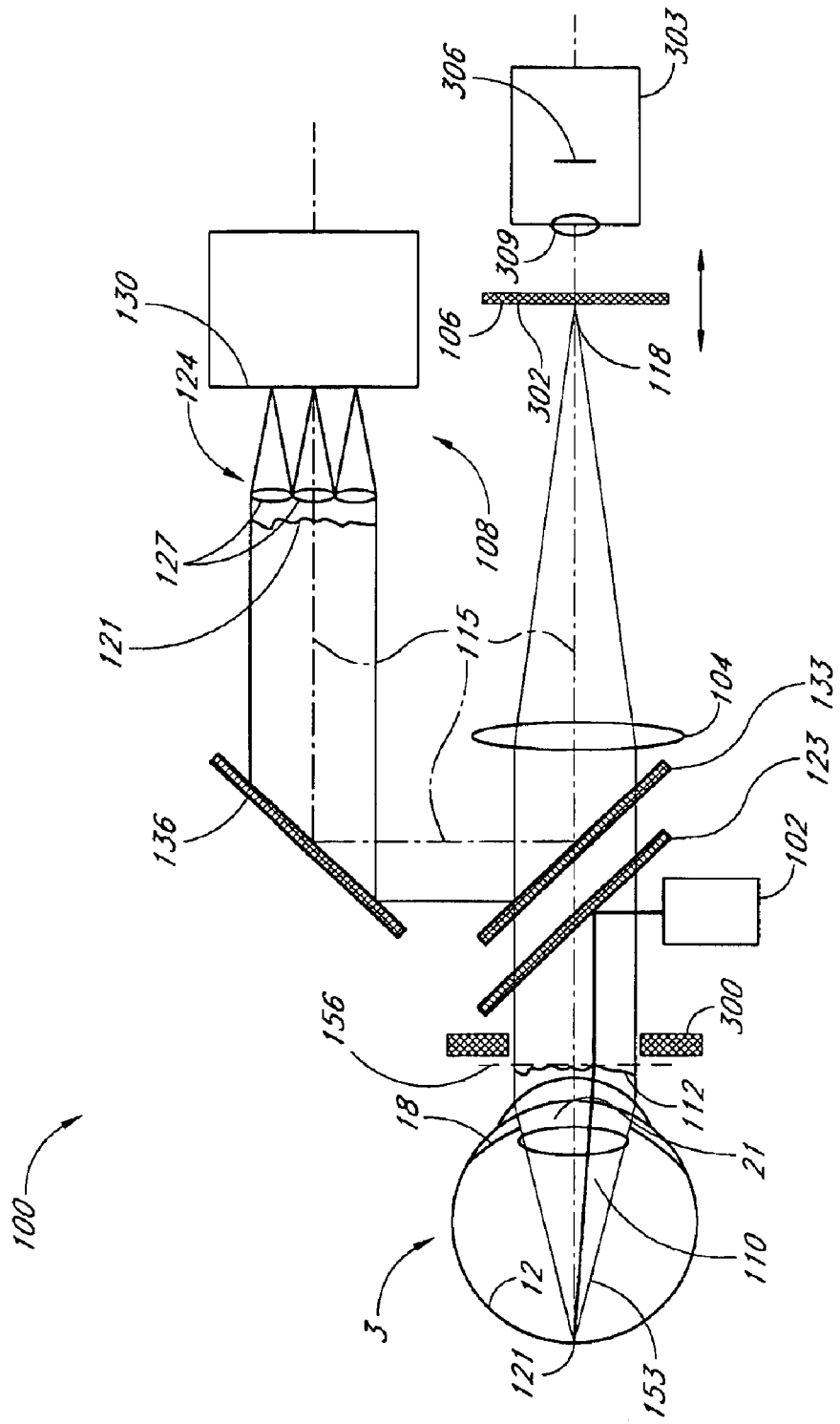
FIG. 5 is a schematic illustration of a device according to embodiments of the invention, wherein a second light source and a camera are used to form an image of the front of an eye.

In certain embodiments, such as that schematically illustrated in FIG. 5, the device 100 further comprises a second light source 300 that is disposed to illuminate pupil 21 of the eye 3. The first light source 102 provides light primarily at a first wavelength $\lambda_1$ and the second light source 300 provides light primarily at a second wavelength $\lambda_2$ different from the first wavelength $\lambda_1$. Preferably, $\lambda_1$ is shorter than $\lambda_2$; however, the device 100 may also be designed and constructed such that $\lambda_2$ shorter than $\lambda_1$. In either case, the reflective surface 106 comprises a dichroic filter 302 that reflects light from the first light source 102 and that transmits light from the second light source 300. Preferably, the dichroic filter 302 reflects at least 10% of the light from the first light source 102 and transmits at least 10% of the light from the second light source 300. More preferably, the dichroic filter 302 reflects at least 90% of the light from the first light source 102 and transmits at least 90% of the light from the second light source 300. Even more preferably, the dichroic filter 302 reflects approximately 100% of the light from the first light source 102 and transmits approximately 100% of the light from the second light source 300.

In certain embodiments, the device 100 further comprises a pupil camera 303 that is adapted to receive light from the second light source 300 that is reflected off at least a portion of the eye 3. Preferably, the pupil camera 303 is adapted to produce an image of at least a portion of the eye 3, herein referred to simply as "the image of the eye 3". Preferably, the pupil camera 303 comprises a two dimensional camera sensor 306, such as a CCD or a CMOS detector array; however, other types of optical sensors or sensor arrays are also possible.

As used herein, term "the image of the eye" or "the image of the eye 3" means an image that comprises at least a portion of the eye 3. The image of the eye may comprise an image of the pupil 21 of the eye 3 or some portion thereof, which may also be referred to as "the image of the pupil" or "the image of pupil 21". Alternatively, the image of the eye may additionally comprise an image of all or a portion of the iris 18. In such embodiments, the term "the image of the pupil" may also include all or a portion of the iris 18 in addition to other parts of the eye 3.

The camera 303 may comprise a camera lens 309 that is adapted to produce the image of the eye 3. Preferably, the camera lens 309 is a commercially available camera lens commonly used with CCD cameras, however, the camera lens 309 may be any commercially available or custom compound lens, lens system, achromat lens, or single element lens capable of producing the image of the eye 3. Optionally, the camera lens 309 may be replaced by different type of optical imaging element suitable such as a mirror, diffractive optical element, or holographic optical element. In certain embodiments, the lens 309 is removed and the image of the eye 3 is produced using other devices or means.

Figure 6:
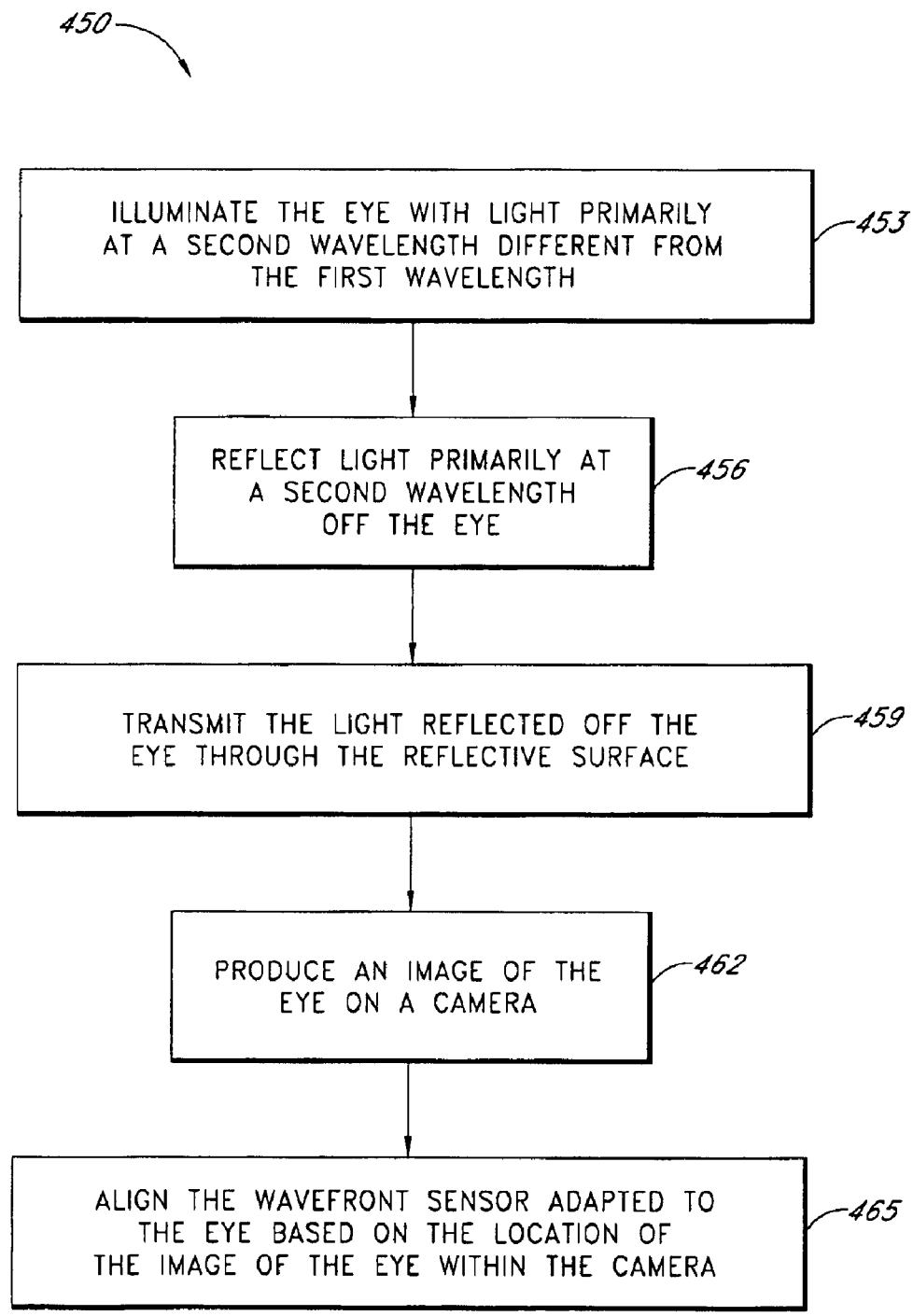
FIG. 6 is a flow diagram of a method for aligning the wavefront sensor to the eye in accordance with embodiments of the present invention.

The pupil camera 303 may be used to provide alignment between the eye 3 to the wavefront sensor 108. For example, FIG. 6 is a flow diagram of a method 450 for aligning the wavefront sensor 108 to the eye 3 in accordance with embodiments of the present invention. The method 450 is exemplary and does not preclude the use of other methods for aligning the wavefront sensor 108 to the eye 3 consistent with embodiments of the present invention.

Referring to FIGS. 5 and 6, the method 450 comprises an operational block 453 which comprises illuminating the eye 3 with light primarily at a second wavelength $\lambda_2$ that is different from the first wavelength $\lambda_1$. The method 450 further comprises an operational block 456 which comprises reflecting light primarily at the second wavelength 2 off the eye 3. The method 450 further comprises an operational block 459 which comprises transmitting the light reflected off the eye 3 through the reflective surface 106. The method 450 further comprises an operational block 462 which comprises producing an image of the eye 3 on the camera 303. In certain embodiments, the image of the eye 3 comprises the pupil 21 of the eye 3. The method 450 further comprises an operational block 465 which comprises providing alignment between the wavefront sensor 108 and the eye 3 based on the image of the eye 3.

In the operational block 453 the eye 3 is illuminated with light primarily at the second wavelength different from the first wavelength . As seen in FIG. 5, light primarily at a second wavelength $\lambda_2$ may be provided by the second light source 300. The second light source 300 is preferably disposed in front of the eye 3 so as to illuminate the eye 3 in a manner conducive to forming an image of the pupil 21 on the two dimensional camera sensor 306.

In the operational block 456 light from the second light source 300 that primarily at the second wavelength $\lambda_2$ is then reflected off the eye 3. The reflected light propagates along the optical path 115 and some portion thereof is transmitted through the various optical components along the optical path 115. The light is collected by the lens 104 and is directed towards the reflective surface 106.

In the operational block 459 the light from the second light source 300 that is reflected off the eye 3 is then transmitted through the reflective surface 106. Preferably, the reflective surface 106 comprises the dichroic filter 302 that is reflective of light at first wavelength $\lambda_1$ and transmissive of light of the second wavelength $\lambda_2$. Light from the first light source 102 is reflected by the dichroic filter 302 and continues along the optical path 115 to form the image 121 of the wavefront 112 as described above herein. Light from the second light source 300 is transmitted by the dichroic filter 302 and is received by the camera 303.

In the operational block 462, an image of the eye 3 is produced on the camera 309 from the light transmitted through the reflective surface 106. The camera lens 309, or an alternative optical imaging element, is selected such that the combination of the lens 104 and the camera lens 309 form the image of the eye 3. In certain embodiments, the image of the eye 3 comprises the pupil 21 and, preferably, at least a portion of the iris 18. In such embodiments, the camera image may comprise a darker area corresponding to the pupil 21 that is contrasted by a surrounding lighter region corresponding to the iris 18.

In the operational block 465 alignment between the wavefront sensor 108 and the eye 3 is provided based on the image of the pupil 21. Once the image of the pupil 21 is obtained, alignment between the wavefront sensor 108 and the eye 3 may be performed using the image of the pupil 21 that is formed on the camera 303. The wavefront sensor 108 may be aligned to the eye 3 by moving the device 100, the eye 3, or both until the image of the pupil 21 is substantially centered in the field of view of the camera 303.

In one embodiment, the alignment procedure is performed manually by observing the position of the image of the pupil 21 on a monitor connected to the camera 303. Alternatively, the alignment procedure may be performed is performed in an automated or semi-automated manner wherein the output from the camera 303 is electronically coupled to a computer or similar device and software is used to determine when alignment is obtained between the eye 3 and the wavefront sensor 108. Once alignment is obtained between the eye 3 and the wavefront sensor 108, data from the wavefront sensor 108 may be saved using a computer or other suitable electronic device.

It will be appreciated that the image of the eye 3 and the image of the pupil 21 formed in the camera 303 may additionally or alternatively be used for other purposes besides alignment of the wavefront sensor 108 and the eye 3, such as the size or shape of the pupil 21. For example, the image of the eye 3 in the camera 303 may provide additional information regarding the eye 3 that may be used in conjunction with information obtained by the wavefront sensor 108. Such additional information might include the presence of certain substances in the eye, the shape of the eye, or obstructions within the area of the pupil. If the light source were a coherent light source, such as a laser, the image of the eye 3 formed in the camera 303 might contain contour information of the cornea 9 or similar type information. In such embodiments, the light from the image of the eye 3 might be combined with another coherent light source to produce interference fringes.

Those skilled in the art will appreciate that the methods and designs described above have additional applications and that the relevant applications are not limited to those specifically recited above. Also, the present invention may be embodied in other specific forms without departing from the essential characteristics as described herein. The embodiments described above are to be considered in all respects as illustrative only and not restrictive in any manner.

What is claimed is:

1. A device for measuring aberrations of an eye, comprising:

a first light source adapted to reflect light off the eye's retina so as to produce a wavefront, the wavefront propagating along an optical path;

a lens disposed along the optical path for receiving the light from the wavefront;

a reflective surface disposed to reflect the light from the wavefront that is received by the lens back through the lens, so as to produce an image of the wavefront; and wherein a wavefront sensor may be adapted to receive the light from the wavefront that is reflected back through the lens so as to provide a measure of the aberrations of the eye;

wherein the device further comprises a second light source disposed to illuminate the eye; the first light source provides light primarily at a first wavelength; and the second light source provides light primarily at a second wavelength different from the first wavelength; and wherein the reflective surface comprises a dichroic filter; light from the first light source is reflected by the reflective surface; and light from the second light source is transmitted through the reflective surface.

2. The device of claim 1, wherein the first light source is a laser.

3. The device of claim 1, wherein the distance between the lens and front of eye is approximately one focal length of the lens.

4. The device of claim 1, wherein the wavefront sensor is a Shack-Hartmann type sensor.

5. The device of claim 1, wherein the reflective surface is disposed at or near a focus of the lens.

6. The device of claim 5, wherein the reflective surface is moveable so as to allow adjustment of the distance between the focus and the reflective surface.

7. The device of claim 1, further comprising a first beamsplitter disposed along the optical path adapted to reflect a portion of light from the first light source and to direct the reflected portion onto the eye's retina.

8. The device of claim 7, wherein the first beamsplitter transmits at least about 50% of the light from the first light source.

9. The device of claim 7, wherein the first beamsplitter transmits at least about 90% of the light from the first light source.

10. The device of claim 7, further comprising wavefront-directing optics.

11. The device of claim 10, wherein the wavefront-directing optics comprise a second beamsplitter disposed along the optical path between the eye and the lens.

12. The device of claim 11, wherein the second beamsplitter is adapted to transmit light from the wavefront propagating from the eye to the second beamsplitter and to reflect light from the wavefront propagating from the reflective surface to the second beamsplitter.

13. The device of claim 11, wherein the wavefront-directing optics further comprise at least one reflector.

14. The device of claim 1, wherein the lens has a focal length approximately 120 millimeters.

15. The device of claim 14, wherein device is contained within an envelop that is no larger than 220 millimeters in length, 70 millimeters in width, and 130 millimeters in height.

16. The device of claim 1, wherein the lens has a focal length approximately 60 millimeters.

17. The device of claim 16, wherein device is contained within an envelop that is no larger than 110 millimeters in length, 35 millimeters in width, and 65 millimeters in height.

18. The device of claim 1, wherein the first wavelength is shorter than the second wavelength.

19. The device of claim 1, wherein the second wavelength is shorter than the first wavelength.

20. The device of claim 1, further comprising a camera adapted to receive light from the second light source reflected off at least a portion of the eye.

21. The device of claim 20, wherein the camera further comprises a camera lens adapted to produce an image of the eye.

22. The device of claim 20, wherein the camera is adapted to produce an image of the eye.

23. The device of claim 22, wherein the image of the eye is used to provide alignment between the wavefront sensor and the eye.

24. The device of claim 22, wherein the image of the eye includes at least a portion of the iris of the eye.

25. method of measuring aberrations of an eye, comprising:

illuminating the eye with light primarily at a first wavelength so as to produce a wavefront that propagates along an optical path;

propagating light from the wavefront through a lens disposed along the optical path;

reflecting the light propagated through the lens off of a reflective surface;

transmitting the light reflected off of the reflective surface back through the lens so as to form an image of the wavefront;

measuring the aberrations of the eye based on the image of the wavefront, wherein the measuring step comprises providing wavefront-directing optics for directing the image of the wavefront to a wavefront sensor for measuring the aberrations of the eye;

illuminating the eye with light primarily at a second wavelength different from the first wavelength;

reflecting light primarily at the second wavelength off the eye;

transmitting the light reflected off the eye through the reflective surface;

producing an image of the eye on a camera; and aligning the wavefront sensor to the eye based on the location of the image of the eye within the camera.

26. The method of claim 25, wherein the wavefront-directing optics comprise a beamsplitter disposed along an optical path between the eye and the lens.

27. The method of claim 26, further comprising reflecting a portion of the light reflected off of the reflective surface.

28. The method of claim 25, further comprising, placing the reflective surface so as to adjust the distance between a focus of the lens and the reflective surface.

29. The method of claim 25, further comprising, placing the reflective surface such that light reflected off of the reflective surface is substantially collimated.

30. The method of claim 25, further comprising, moving the reflective surface so as to compensate for an ocular defocus.

* * * * *

UNITED STATES PATENT AND TRADEMARK OFFICE
CERTIFICATE OF CORRECTION

PATENT NO. : 6,988,801 B2
APPLICATION NO. : 10/397101
DATED : January 24, 2006
INVENTOR(S) : Geunyoung Yoon Page 1 of 1

It is certified that error appears in the above-identified patent and that said Letters Patent is hereby corrected as shown below:

Column 11, Line 29, After "wavelength" delete "2", and insert -- $\lambda_2$ --

Column 14, Line 17 (approx.), Before "method" insert --A--

Signed and Sealed this

Tenth Day of April, 2007

JON W. DUDAS
*Director of the United States Patent and Trademark Office*